United States Patent
Xu et al.

(10) Patent No.: US 8,926,808 B2
(45) Date of Patent: Jan. 6, 2015

(54) VERSATILE ELECTROCHEMICAL PAPER-IMMUNOSENSOR AND METHOD FOR DETECTION OF AMINOGLYCOSIDE ANTIBIOTICS BY USING THE SENSOR

(75) Inventors: Chuanlai Xu, Wuxi (CN); Libing Wang, Wuxi (CN); Xiaoling Wu, Wuxi (CN); Hua Kuang, Wuxi (CN); Wei Chen, Wuxi (CN); Wei Ma, Wuxi (CN)

(73) Assignee: Jiangnan University, Jiangsu Province (CN)

( * ) Notice: Subject to any disclaimer, the term of this patent is extended or adjusted under 35 U.S.C. 154(b) by 0 days.

(21) Appl. No.: 13/304,496

(22) Filed: Nov. 25, 2011

(65) Prior Publication Data

US 2012/0325681 A1 Dec. 27, 2012

(30) Foreign Application Priority Data

Jun. 27, 2011 (CN) .......................... 2011 1 0173954

(51) Int. Cl.
*G01N 33/487* (2006.01)
*B82Y 30/00* (2011.01)
*G01N 33/53* (2006.01)
*G01N 33/543* (2006.01)
*G01N 33/551* (2006.01)

(52) U.S. Cl.
CPC ............ *B82Y 30/00* (2013.01); *G01N 33/5308* (2013.01); *G01N 33/5438* (2013.01); *G01N 33/551* (2013.01)
USPC .................. 204/403.02; 205/792; 204/403.01

(58) Field of Classification Search
CPC .................................. G01N 27/3271–27/3278
USPC ............ 204/403.01–403.15, 400; 205/777.5, 205/775, 792
See application file for complete search history.

(56) References Cited

PUBLICATIONS

Ye Zhu, Jung Ik Son, Yoon-Bo Shim, Amplification strategy based on gold nanoparticle-decorated carbon nanotubes for neomycin immunosensors, Biosensors and Bioelectronics, vol. 26, Issue 3, Nov. 15, 2010, pp. 1002-1008.*
Libing Wang, Wei Chen, Dinghua Xu, Bong Sup Shim, Yingyue Zhu, Fengxia Sun, Liqiang Liu, Chifang Peng, Zhengyu Jin, Chuanlai Xu, and Nicholas A. Kotov Simple, Rapid, Sensitive, and Versatile SWNT—Paper Sensor for Environmental Toxin Detection Competitive with ELISA, Nano Letters 2009 9 (12), 4147-4152.*
Zhao, By Yanfang, et al. "Label-free electrochemical immunosensor for sensitive detection of kanamycin." Sensors and Actuators B: Chemical 155.2, pp. 618-625 (2011).*

* cited by examiner

*Primary Examiner* — Luan Van
*Assistant Examiner* — Maris R Kessel
(74) *Attorney, Agent, or Firm* — Jacobson Holman Hershkovitz PLLC; Jiwen Chen

(57) ABSTRACT

An electrochemical paper-immunosensor and method for detecting aminoglycoside antibiotics is developed in the present invention. Single-walled carbon nanotubes are coated on the common filtration paper by dip-dry cycles. With antibody against neomycin adding to the coating solution, a high sensitive biosensor for specific detection of neomycin is prepared, satisfying to the rigid authority regulations. The sensor is not only sensitive but also rapid, comparing with the classic ELISA method, with LOD of 0.04 ng mL$^{-1}$ and the whole detection process lasting less than 30 min. Another notable advantage of this invention is the versatility of the sensor, similar method is engaged to prepare the versatile sensor for other aminoglycoside antibiotics, replacement with relevant antibodies.

1 Claim, 1 Drawing Sheet

VERSATILE ELECTROCHEMICAL PAPER-IMMUNOSENSOR AND METHOD FOR DETECTION OF AMINOGLYCOSIDE ANTIBIOTICS BY USING THE SENSOR

The present application claims the priority of Chinese Application No. 201110173954.9, filed Jun. 27, 2011 under 35 U.S.C. §119, which is hereby incorporated by reference.

TECHNICAL FIELD

The present invention relates to preparation of a versatile electrochemical immunosensor and method for detection of aminoglycoside antibiotics, such as neomycin. It belongs to food safety detection field.

BACKGROUND OF THE INVENTION

With the development of modern husbandry, widespread abuse of antibiotics, leading to the residues of antibiotics in livestock products, has become not only a potential threat to the public health, but also one of critical factors influencing on the international trade of foodstuffs of animal origin. Moreover, antimicrobial residues may inhibit starter cultures for cheese and yoghurt production in the dairy industry. Hence, it is essential to effectively control and analyze aminoglycoside antibiotics residues in milk.

The maximum residue limits (MRLs) are laid down in the commission regulation No. 2377/90 within the European Union, are listed in Title 21, Part 556 (21 CFR 556) set by the United States Food and Drug Administration, and are established in No. 235/2002 by the Ministry Agriculture of China, as well as similar regulations in other countries.

For the detection of antibiotic residues in milk, LC, HPLC methods, immunoassays as well as modified-RNA aptamer-based sensors have been developed for the quantification of aminoglycoside antibiotics, but these methods are time-consuming, expensive or lack sensitivity, not suitable for the fast on-site analysis. Besides the present analysis methods for antibiotics, the rigid control of residues of antibiotics situation also make the detection of aminoglycoside antibiotics a challenging problem.

Nano-materials are a kind of new materials with specific functions. More and more researches have focus on establishing relevant rapid and high sensitive methods based on the characteristics of nano-materials. Since first discovered by the Japanese scientists Ijima, Carbon nanotubes have attracted the people's great attention due to its unique structural characteristics and electrical properties, and lots of sensors based on carbon nanotube has been developed and more are under development. However, high-cost and difficulty to use limit the practical application of the developed sensor.

In the present invention, a sensitive, rapid, simple, and low-cost electrochemical immunosensor to detect the aminoglycoside antibiotics based on paper has been developed. The detection is very fast, lasting within 30 min. And this method also shows good sensitivity and can also be applied for other aminoglycoside antibiotics analysis following similar procedures.

SUMMARY OF THE INVENTION

Accordingly, the invention is to prepare a rapid, highly sensitive and low-cost sensor for detection of neomycin in milk.

The invention also establishes the method and technical parameters for the fast and sensitive neomycin analysis by using this sensor.

Based on the two former purposes, the invention also provides the preparation of versatile aminoglycosides antibiotics biosensors and their corresponding detection methods for practical application.

The present invention provides the preparation method for neomycin immunosensor, which involves coating the carbon nanotubes on the typical filter paper through dip-dry method. Before coating, the antibodies against neomycin are added into the coating solution, thus we can obtain the specific biosensor for the determination of neomycin. And the preparation method comprises:

a) Single-walled carbon nanotubes (SWNTs) are well dispersed in poly(sodium 4-styrenesulfonate) (PSS), and the concentration of SWNTs is maintained about 3-27 mg/mL. Ultrasonication is used to make sure the good dispersity of the coating solution;

b) A certain amount of antibody is added into the well-dispersed carbon nanotubes-PSS solution, with a final concentration of 3-15 µg/mL;

c) Filtration paper is cut into small pieces with fixed dimension of 4×0.5 cm, followed by dipping in the coating solution and freeze-dry under vacuum. The paper is subject to the 10-15 times dip-dry cycles to obtain sufficient conductivity. And then, the prepared paper sensors are stored under 4° C.

The application of the sensor for rapid detection of neomycin is based on the current variation of the carbon nanotube-paper composites.

The fabricated paper sensors function as the working electrode, Pt wire and Ag/AgCl are used as counter and reference electrodes, respectively. The current values against time (i-t curves) are recorded by performing a chronoamperometry method on the electrochemical workstation. With addition different concentration of neomycin standard solution, the current change through the whole paper sensor is recorded as the signal, and then we can obtain a calibration curve of current changes against relevant concentration of neomycin. Thus, we can easily determine the residues of neomycin of the really milk samples.

Besides the sensor for neomycin detection, we can also fabricate versatile aminoglycoside antibiotics analysis sensors. The fabrication procedures and detection methods are exactly the same as the sensor specific to neomycin, only replacement with corresponding antibodies.

In conclusion, the present invention comprises the following three main points:

a) Fabrication of carbon nanotubes-paper composites sensor specific to neomycin by dip-dry method;

b) Establishing the analysis method for rapid and sensitive detection of neomycin based on the changes of the conductivity of the sensor;

c) Establishing versatile aminoglycoside antibiotics sensors and analysis methods with adding into relevant antibodies.

The quantification determination results show that the sensor is sensitive to neomycin with a LOD of 0.04 ng/mL, which satisfies the rigid authorities regulations. Moreover, the sensor is rapid comparing with typical ELISA method, with the whole detection procedure lasting within 30 min. In addition, other similar aminoglycoside antibiotics sensors can be prepared following similar procedures with adding into relevant antibodies.

Generally speaking, the present invention provides the methods for preparation of versatile, rapid, and sensitive sensors for aminoglycoside antibiotics and can be applied to real milk samples analysis.

DETAILED DESCRIPTION OF THE INVENTION

Figure 1:
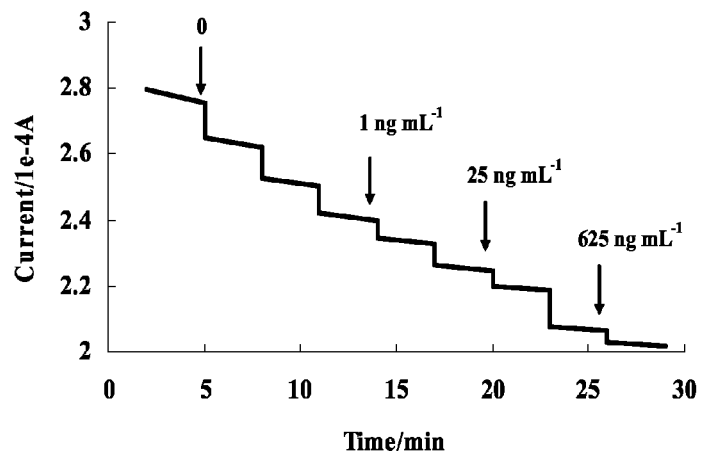
FIG. 1 shows the signal curves of current values against time based on the sensor specific to neomycin. A LOD of 0.04 ng/mL is easily observed, which shows the high sensitivity for neomycin detection by using this sensor.
Figure 2:
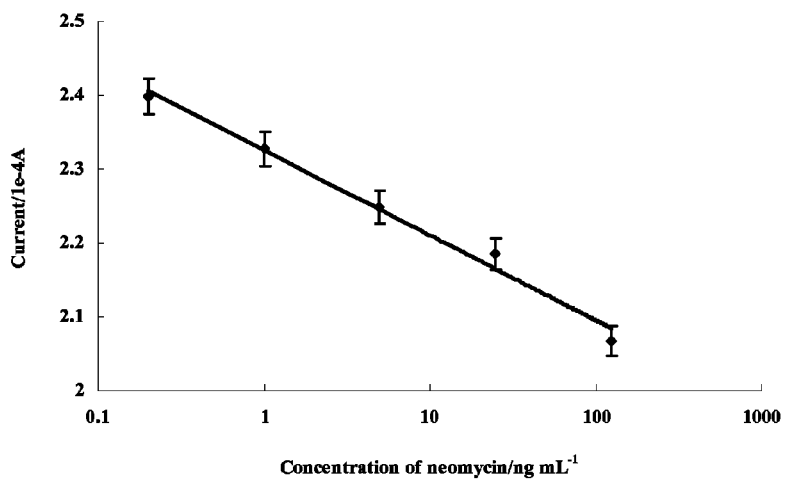
FIG. 2 displays the calibration curves for neomycin detection. It indicates that an excellent linear working range from 0.2 to 125 ng/mL.

The detailed information of the invention is further described through the steps listed in the following text. All the reagents involved are analytical grade purify. Notably to mention that the following detailed steps are as exemplifications, while the present invention is not limited to the content as follows:

Step 1 Single-walled carbon nanotubes (SWNTs) are well dispersed in poly(sodium 4-styrenesulfonate) (PSS), and the concentration of SWNTs is maintained about 3-27 mg/mL. Ultrasonication is used to make sure the good dispersity of the coating solution;

Step 2 A certain amount of antibody is added into the well-dispersed carbon nanotubes-PSS solution, with a final concentration of 3-15 µg/mL;

Step 3 Filtration paper is cut into small pieces with fixed dimension of 4×0.5 cm, followed by dipping in the coating solution and freeze-dry under vacuum. The paper is subject to the 10-15 times dip-dry cycles to obtain sufficient conductivity. And then, the prepared paper sensors are stored under 4° C.;

Step 4 The fabricated paper sensors function as the working electrode, Pt wire and Ag/AgCl are used as counter and reference electrodes, respectively. The i-t curves are recorded by performing a chronoamperometry method on the electrochemical workstation;

Step 5 Optimize the buffer solution for detection system, choose the one which obtain the strongest current signal;

Step 6 Optimize the pH of the chosen buffer solution according to steps e, the appropriate pH should achieve the high current;

Step 7 Optimize the temperature of detection system, the best current responses are expected under the suitable temperature;

Step 8 The i-t curves are recorded following the adding of relevant amount of neomycin;

Step 9 A calibration curve is established according to the relationship of concentration of neomycin and the balanced current values from the transient plateau of i-t curves;

Step 10 According to corresponding conditions described above, the sensors are then used to analysis the residues of neomycin in milk samples;

Step 11 Establish versatile sensors specific to other aminoglycoside antibiotics, replacement with relevant antibodies;

Step 12 Optimize the analytical parameters of the versatile sensors to establish the detection methods for applications, referring to neomycin sensors described above.

The invention claimed is:

1. An electrochemical paper-immunosensor sensitive to neomycin in milk products comprising:
 a paper substrate;
 an electrode comprising:
  a biosensor layer with carbon nanotubes incorporated with antibodies against neomycin in milk products formed on the substrate;
 a counter electrode formed on the substrate; and
 a reference electrode formed on the substrate;
wherein final concentration of the antibodies against neomycin in milk products is maintained at 5.8 µg/mL, and final concentration of the carbon nanotubes dispersed in poly(sodium 4-styrenesulfonate) (PSS) solution is maintained at 22 mg/mL; and wherein a number of dip-dry cycles, defined as the number of SWNT layers coated, is 11; and wherein the electrochemical paper-immunosensor is sensitive to neomycin with a limit of detection of 0.04 ng/mL.

* * * * *